United States Patent [19]

Girardot

[11] Patent Number: 5,620,694
[45] Date of Patent: Apr. 15, 1997

[54] LAMINATED DUAL TEXTURED TREATMENT PADS

[75] Inventor: Richard M. Girardot, Cincinnati, Ohio

[73] Assignee: The Procter & Gamble Company, Cincinnati, Ohio

[21] Appl. No.: 433,597

[22] Filed: May 3, 1995

Related U.S. Application Data

[63] Continuation of Ser. No. 236,869, Apr. 29, 1994, abandoned, which is a continuation of Ser. No. 104,233, Aug. 10, 1993, abandoned, which is a continuation of Ser. No. 919,678, Jul. 27, 1992, abandoned.

[51] Int. Cl.⁶ .................................................. A01N 25/34
[52] U.S. Cl. .................... 424/402; 424/443; 428/219; 514/859; 442/412
[58] Field of Search .................... 424/402, 443; 428/219, 233; 514/859

[56] References Cited

U.S. PATENT DOCUMENTS

| | | | |
|---|---|---|---|
| 3,180,782 | 4/1965 | Coates | 428/233 |
| 3,485,706 | 12/1969 | Evans | 161/72 |
| 3,498,874 | 3/1970 | Evans et al. | 161/109 |
| 3,778,341 | 12/1973 | Plummer et al. | 162/125 |
| 4,355,028 | 10/1982 | Kligman | 514/859 |
| 4,379,799 | 4/1983 | Holmes et al. | 428/131 |
| 4,546,027 | 10/1985 | Holvoet | 428/219 |
| 4,608,370 | 8/1986 | Aronsohn | 514/159 |
| 4,610,352 | 9/1986 | Howey et al. | 206/313 |
| 4,612,226 | 9/1986 | Kennette et al. | 428/134 |
| 4,636,418 | 1/1987 | Kennard et al. | 428/110 |
| 4,737,404 | 4/1988 | Jackson | 428/284 |
| 4,774,124 | 9/1988 | Shimalla et al. | 428/171 |
| 4,797,310 | 1/1989 | Barby | 428/71 |
| 4,891,227 | 1/1990 | Thamen et al. | 424/443 |
| 4,891,228 | 1/1990 | Thaman et al. | 424/443 |
| 4,925,722 | 5/1990 | Jeffers et al. | 428/131 |
| 4,959,894 | 10/1990 | Jeffers et al. | 28/104 |
| 4,960,630 | 10/1990 | Greenway et al. | 428/131 |
| 4,995,151 | 2/1991 | Siegel et al. | 26/69 |
| 5,017,367 | 5/1991 | Stojkoski | 424/63 |
| 5,098,519 | 3/1992 | Ramasubramanian | 162/109 |
| 5,204,165 | 4/1993 | Schortmann | 428/198 |
| 5,302,446 | 4/1994 | Horn | 428/286 |

FOREIGN PATENT DOCUMENTS

| | | | |
|---|---|---|---|
| 89/10441 | 11/1989 | WIPO | D04H 11/46 |

*Primary Examiner*—D. Gabrielle Phelan
*Attorney, Agent, or Firm*—Anthony D. Sabatelli; David K. Dabbiere

[57] ABSTRACT

The present invention relates to dual textured treatment pads comprising at least one paper pad layer laminated to at least one nonwoven, synthetic fiber pad layer. The invention also encompasses treatment pads impregnated with a suitable medicated, cleansing, or cosmetic composition. The invention further encompasses a method of treating acne and skin wrinkling and/or atrophy with these medicated pads.

15 Claims, No Drawings

LAMINATED DUAL TEXTURED TREATMENT PADS

This is a continuation of application Ser. No. 08/236,869, filed on Apr. 29, 1994, now abandoned, which is a continuation of application Ser. No. 08/104,233, filed Aug. 10, 1993, now abandoned, which is a continuation of application Ser. No. 07/919,678, filed Jul. 27, 1992, now abandoned.

TECHNICAL FIELD

The present invention relates to dual textured treatment pads comprising at least one paper pad layer laminated to at least one nonwoven, synthetic fiber pad layer. The nonwoven pad layer can comprise a textured repeating pattern having at least two adjacent delineated regions simultaneously not having the same mean thickness, wherein the first region has a mean thickness from about 0.025 cm to about 0.30 cm and the second region has a mean thickness from about 0.010 cm to about 0.050 cm. In other embodiments, the nonwoven pad layer can comprise an apertured, textured, repeating pattern.

The invention also encompasses cleansing or treatment pads which comprise the dual textured pads of the instant invention impregnated with a suitable medicated, cleansing, or cosmetic composition.

The invention also encompasses a method for treating acne in humans comprising topically applying to the affected area a medicated pad of the present invention.

BACKGROUND OF THE INVENTION

It is highly desirable to deliver cleansing products or products for treating disorders of the skin (e.g., acne) from a single use disposable pad. Disposable pads are both convenient and sanitary to use. However, current disposable pads have limitations.

Most disposable pads comprise a single layer having a single textured surface and cannot provide both gentle and vigorous cleansing from the same pad. Moreover, many single layered pads lack the rigidity and integrity required for effective cleansing and/or treatment. The rigidity and integrity of these pads can be improved by increasing their thickness or by laminating them to a second nonwoven pad layer to form a dual layered nonwoven pad. However, these dual layered pads are not very cost effective for onetime use. Also known are dual layered pads which comprise a paper pad layer laminated to a high-loft nonwoven pad layer. However, these dual layered pads are still relatively expensive for one time use. Therefore, it would be highly desirable to develop treatment pads having two differently textured surfaces, which have sufficient rigidity and integrity, and which are also cost effective.

It has been found herein that by laminating a relatively low cost paper pad layer to a nonwoven synthetic fiber pad layer having a low basis weight (and also a relatively low cost) that a dual textured pad can be produced having improved strength and rigidity, textural variety from side to side, and cost effectiveness. The nonwoven pad layer can comprise a repeating textured pattern having at least two adjacent delineated regions of different thicknesses. Alternatively, the nonwoven pad layer can have an apertured, textured, repeating pattern.

The pattern of the nonwoven layer provides a macroscopic texture that is smoother and less irritating to the skin than more expensive high-loft nonwovens. Also, because the nonwoven layer is laminated to a paper layer, a less rigid and lower cost nonwoven can be employed to achieve a finished pad having good rigidity and durability in comparison to a single layer nonwoven pad.

The dual textured pads of the instant invention allow for one side to be used, for example, for scrubbing and the other for gentle cleansing. Furthermore, the patterned or apertured side of these dual-sided pads tend to concentrate removed soil and dirt on the raised areas, thereby enhancing the user's perception of cleansing efficacy. Also, the dual sided pads can be manufactured in which the layers are of different colors, thereby helping the user to further distinguish the surfaces.

The treatment pads of the instant invention are useful for delivering a wide variety of cleansing compositions, pharmaceutical actives, and cosmetics, including astringents, toners, lotions, emulsions, moisturizers, and the like. These pads are especially well suited for delivering cleansers and compositions for the treatment of acne. These pads are also useful for delivering compositions for the regulation of skin wrinkles and/or atrophy. Also, these pads are useful for make-up removal.

It is therefore an object of the present invention to provide dual textured treatment pads having improved efficacy and aesthetics, and yet which are also cost effective and durable. Another object of the present invention is to provide dual textured treatment pads comprising at least one paper pad layer laminated to at least one nonwoven synthetic fiber pad layer in which the nonwoven layer comprises a repeating textured pattern having at least two adjacent delineated regions simultaneously not having the same mean thickness. Yet another object of the present invention is to provide dual textured treatment pads comprising at least one paper pad layer laminated to at least one nonwoven synthetic fiber pad layer having an apertured, textured, repeating pattern. Still another object of the present invention is to provide treatment pads which contain a medicated composition. A further object of the present invention is to provide a method for treating acne in mammalian skin employing a medicated pad. An even further object of the present invention is to provide a method for regulating skin wrinkles and/or atrophy in mammalian skin employing a medicated pad. A still further object of the present invention is to provide a method for delivering a wide variety of skin care products to human skin.

These and other objects of this invention will become apparent in light of the following disclosure.

SUMMARY OF THE INVENTION

The present invention relates to a dual textured laminated treatment pad comprising:

(a) at least one paper layer having a basis weight from about 35 gsy to about 155 gsy and a thickness from about 0.045 cm to about 0.30 cm, and (b) at least one synthetic fiber, nonwoven layer having a basis weight from about 20 gsy to about 105 gsy, having a repeating pattern comprising at least two adjacent delineated regions simultaneously not having the same mean thickness, wherein said first region has a mean thickness from about 0.025 cm to about 0.30 cm and said second region has a mean thickness from about 0.010 cm to about 0.050 cm, whereby said paper layer is positioned parallel to and in contact with said synthetic nonwoven layer.

Alternatively, the present invention relates to a dual textured laminated treatment pad comprising:

(a) at least one paper layer having a basis weight from about 35 gsy to about 155 gsy and a thickness from about 0.045 cm to about 0.30 cm, and (b) at least one apertured, synthetic fiber, nonwoven layer having a basis weight from about 20 gsy to about 105 gsy, whereby said paper layer is positioned parallel to and in contact with said synthetic nonwoven layer.

The present invention also relates to medicated cleansing pads which comprise a dual textured treatment pad containing a medicated composition.

In yet further embodiments, the present invention also relates to a method for treating acne in mammalian skin comprising treating the skin with these medicated pads, and to a method for regulating skin wrinkling and/or atrophy in mammalian skin comprising treating the skin with these medicated pads.

All percentages and ratios used herein are by weight and all measurements are at 25° C., unless otherwise indicated.

DETAILED DESCRIPTION OF THE INVENTION

Definitions

The term "apertured", as used herein means a pad layer which has holes or openings punctuating its surface.

The term "basis weight", as used herein is the weight per unit area of a fabric or pad. Typically, basis weights are reported in grams per square yard, which is abbreviated as "gsy".

The term "denier", as used herein, describes a unit of fineness for a fiber equal to the weight of 9000 meters of the fiber. For example, a 100 denier fiber would have a weight of 100 grams per 9000 meters. See H. Bennett, *Concise Chemical and Technical Dictionary, Fourth Enlarged Edition*, p. 384 (1986), which is incorporated by reference herein.

The term "a repeating pattern comprising at least two adjacent delineated regions simultaneously not having the same mean thickness", as used herein, means that the nonwoven layer of the pads of the instant invention can be textured with a pattern, in which there are at least two different areas which have different mean cross-sectional caliper thicknesses.

The term "hydroentangled nonwoven", as used herein, describes a nonwoven material made by a manufacturing process that entangles the fibers of one or more webs together by using a series of water jets to increase the finished product's integrity. The term "hydro- entangled nonwoven" is also known by the following synonyms: spunlace nonwoven, jet entangled nonwoven, and hydrologically needled fabric. See, M. Wilharm, "Spunlaced Nonwovens", *Nonwovens Industry*, vol. 22, no. 12, December 1991, pp. 48–49, which is incorporated by reference herein in its entirety.

The terms "laminate" and "laminated" are used herein to describe pads comprising two or more superposed layers which are held together by an adhesive or mechanical means. The layers are positioned parallel to and in contact with each other. See *Webster's Ninth New Collegiate Dictionary*, p. 671, (1983), which is incorporated by reference herein.

The term "loft", is used herein to describe the springiness of a fabric, layer, or pad returning to its normal position after compression. See H. Bennett, *Concise Chemical and Technical Dictionary, Fourth Enlarged Edition*, p. 711 (1986), which is incorporated by reference herein.

The term "thermally bonded" or "thermo-bonded", as used herein, means that either the pad layers and/or the fibers therein are bonded or fused together in a process employing heat and any optional resins, binders, adhesives, and the like.

The term "thermally formed texture", as used herein, means a pad that is embossed or formed with a pattern or texture by the application of heat and a suitable forming device. Nonlimiting examples of forming devices include dies, molds, screens, meshes, rollers, and the like.

DUAL TEXTURED TREATMENT PADS

The dual textured treatment pads of the present invention comprise at least one paper pad layer laminated to at least one nonwoven, synthetic fiber pad layer. The dual textured pads of the instant invention include the following essential as well as optional components.

Paper Layer

The dual textured pads of the instant invention comprise at least one paper layer. By paper is meant a fibrous web or sheet composed of plant derived fibers, i.e. cellulosic fibers. These webs or sheets are most commonly formed on a fine wire screen from a liquid suspension of the fibers. See C. A. Hampel et al., *The Encyclopedia of Chemistry, Third Edition*, 1973, pp. 793–795 (1973); *The Encyclopedia Americana*, vol. 21, pp. 376–383 (1984); and G. A. Smook, *Handbook for Pulp and Paper Technologists*, third edition, Technical Association for the Pulp and Paper Industry (1986); which are incorporated by reference herein.

The paper layer is composed of cellulosic fibers selected from the group consisting of wood pulp fibers, cotton fibers, hemp fibers, jute fibers, flax fibers, and mixtures thereof.

Alternatively, the paper layer of the pads of the instant invention can be obtained from a wide variety of commercial sources. Nonlimiting examples of suitable commercially available paper layers useful herein include Airtex®, an embossed airlaid paper having a caliper thickness of about 0.035 inches (0.089 cm), and a basis weight of about 71 gsy, available from James River, Green Bay, Wis.; and Walkisoft®, an embossed airlaid paper having a caliper thickness of about 0.035 inches (0.089 cm), and a basis weight of about 75 gsy, available from Walkisoft U.S.A., Mount Holly, N.C.

The paper layer of the dual textured pads of the instant invention can have a thickness of from about 0.045 cm to about 0.30 cm, preferably from about 0.065 cm to about 0.20 cm, and most preferably from about 0.070 cm to about 0.11 cm. These paper layers can have a basis weight of from about 35 gsy to about 155 gsy, preferably from about 45 gsy to about 110 gsy, and most preferably from about 60 gsy to about 100 gsy.

The paper pad layer can be of a wide variety of textures and patterns. Optionally, the paper layer can be colored to provide additional variety. Any standard dyeing or pigmenting techniques and any conventional dyes, pigments, and fixatives can be employed.

Nonwoven Synthetic Fiber Layer

The dual textured pads of the instant invention comprise at least one textured, nonwoven, synthetic fiber layer. By nonwoven is meant that the layer is comprised of fibers which are not woven into a fabric but rather are formed into a sheet, mat, or pad layer. The fibers can either be random (i.e. randomly aligned) or they can be carded (i.e. combed to be oriented in primarily one direction). Furthermore, the nonwoven layer can be composed of a combination of layers of both random and carded fibers.

By synthetic fiber is meant that the fibers are obtained primarily from various man-made materials or from natural materials which have been further altered. The conventional base starting material for the majority of these nonwoven fabrics is usually a fibrous web comprising any of the common synthetic textile-length fibers, or mixtures thereof. Nonlimiting examples of synthetic fibers useful in the instant invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, and mixtures thereof. Examples of some of these fibers include acrylics such as acrilan, creslan, and the acrylonitrile-based fiber, orlon; cellulose ester fibers such as cellulose acetate, arnel, and acele; polyamides such as the nylons (e.g. nylon 6, nylon 66, nylon 610, and the like); polyesters such as fortrel, kodel, and the polyethylene terephthalate fiber, dacron; polyolefins such as polypropylene; and mixtures thereof. Preferred herein are fibers selected from the group consisting of acrylic fibers, nylon fibers, polyester fibers, polypropylene fibers, rayon fibers, and mixtures thereof. These and other suitable fibers and the nonwoven materials prepared therefrom are generally described in Riedel, "Nonwoven Bonding Methods and Materials", *Nonwoven World* (1987); *The Encyclopedia Americana*, vol. 11, pp. 147–153, and vol. 26, pp. 566–581 (1984); U.S. Pat. No. 4,891,227, to Thaman et al., issued Jan. 2, 1990; and U.S. Pat. No. 4,891,228, to Thaman et al., issued Jan. 2, 1990; which are all incorporated by reference herein.

In addition to the synthetic fibers discussed above, the synthetic nonwovens can also comprise from about 0.01% to about 10% of cellulosic fibers selected from the group consisting of wood pulp fibers, cotton fibers, hemp fibers, jute fibers, flax fibers, and mixtures thereof.

Optionally, the synthetic fiber nonwoven layer can be colored to provide additional variety. Any standard dyeing or pigmenting techniques and any conventional dyes, pigments, and fixatives can be employed.

The nonwoven layer of the dual textured pads of the instant invention can have a basis weight of from about 20 gsy to about 105 gsy, preferably from about 25 gsy to about 90 gsy, and most preferably from about 30 gsy to about 80 gsy.

The nonwoven layer of the instant invention can comprise a repeating pattern of at least two adjacent delineated regions in which the first region has a mean thickness from about 0.025 cm to about 0.30 cm, preferably from about 0.030 cm to about 0.15 cm, and most preferably from about 0.035 cm to about 0.095 cm, and in which the second region has a mean thickness from about 0.010 cm to about 0.050 cm, preferably from about 0.012 cm to about 0.035 cm, and most preferably from about 0.015 cm to about 0.025 cm. Alternatively, the nonwoven layer can have a series of regularly or irregularly spaced apertures or voids. Furthermore, in any of the embodiments, the nonwoven layer can also comprise raised nubs or bumps. When the nonwoven layer contains apertures, these apertures are preferably regularly spaced and each have an area from about 0.15 $mm^2$ to about 4.1 $mm^2$, more preferably from about 0.20 $mm^2$ to about 2 $mm^2$, and most preferably from about 0.20 $mm^2$ to about 1.4 $mm^2$. The apertures, when present, comprise from about 1% to about 50%, preferably from about 5% to about 40%, and most preferably from about 8% to about 35% of the total surface area of said nonwoven layer.

Generally, the nonwoven layers can be made by standard air-laying or water-laying processes in which the fibers or filaments are first cut to the desired lengths from long strands, passed into a water or air stream, and then deposited onto a screen or mesh through which the fiber-laden air or water is passed. The resulting nonwoven layer, regardless of its method of production or composition, is then subjected to at least one of several types of bonding operations to anchor the individual fibers together to form a self-sustaining web. In the present invention the nonwoven layer can be prepared by a variety of processes including hydroentanglement, thermally bonding or thermo-bonding, and combinations of these processes.

The nowoven pad layers of the instant invention can be prepared by conventional hydroentanglement processes wherein webs of nonwoven fibers are treated with high pressure fluids while being supported on apertured patterning screens. See U.S. Pat. No. 4,995,151, to Siegel et al., issued Feb. 26, 1991; U.S. Pat. No. 4,960,630, to Greenway et al., issued Oct. 2, 1990; U.S. Pat. No. 4,959,894, to Jeffers et al., issued Oct. 2, 1990; U.S. Pat. No. 4,925,722, to Jeffers et al., issued May 15, 1990; U.S. Pat. No. 4,379,799 to Holmes et al., issued Apr. 12, 1983; U.S. Pat. No. 3,498,874, to Evans et al., issued Mar. 3, 1970; U.S. Pat. No. 3,485,706, to Evans, issued Dec. 23, 1969; and WO Patent No. 89/10441, to Sternlieb et al., published Nov. 2, 1989; all of which are incorporated herein by reference in their entirety.

The nowoven pad layers of the instant invention can also be prepared using a conventional thermal or heat process in which the fibers are thermally formed into a textured pad layer. This process is known as thermal bonding, thermo-bonding, thermal forming, and other names. In this process, a wide variety of textures or patterns can be incorporated into the pad layer employing devices including dies, molds, screens, meshes, rollers, and the like. See U.S. Pat. No. 4,774,124, to Shimalla et al., issued Sep. 27, 1988, which is incorporated by reference herein in its entirety.

Optionally, the nonwoven material can also be treated with a suitable polymeric resin or binder in order to fortify the bonding of the fibers. The polymeric resin or binder helps to provide additional loft and rigidity, and can also provide some resistance to abrasion. Examples of polymeric resins or binders useful herein include those comprising monomers selected from the group consisting of styrene monomers, derivatized styrene monomers, butadiene monomers, derivatized butadiene monomers, and mixtures thereof. Especially preferred for use herein as polymeric resins or binders are styrene-butadiene polymers, examples of which are 76 RES 4305 (a polymer having a styrene to butadiene ratio of 45:55, commercially available from Unocal), Tylac 68-500 (a polymer having a styrene to butadiene ratio of 80:20, commercially available from Reichhold); Gen Flo 3060 (available from Diversitech General, Akron, Ohio); and Union 76 Res 5550 (a 45:55 carboxylated styrene butadiene resin available from Union 76). See U.S. Pat. No. 4,891,227, to Thaman et al., issued Jan. 2, 1990; U.S. Pat. No. 4,891,228, to Thaman et al., issued Jan. 2, 1990, U.S. Pat. No. 4,612,226, to Kennette et al., issued Sep. 16, 1986; U.S. Pat. No. 3,778,341, to Plummer et al., issued Dec. 11, 1973; *Introduction to Polymer Science and Technology: An SPE Textbook*, H. S. Kaufman et al., John Wiley & Sons, New York (1977); *Principles of Polymerization*, G. Odian, John Wiley & Sons, New York (1981); and *Block Copolymers Overview and Critical Survey*, A. Noshay et al., Academic Press, New York (1977), which are all incorporated by reference herein in their entirety.

As with the paper layers described above, the nonwoven synthetic fiber layer of the pads of the instant invention can be obtained from a wide variety of commercial sources. Nonlimiting examples of suitable nonwoven layer materials useful herein include HEF 140-037, an apertured hydroentangled material containing about 50% rayon and 50% polyester, and having a basis weight of about 43 gsy, available from Veratec, Inc., Walpole, Mass.; Novonet® 149-616, a thermo-bonded grid patterned material containing about 100% polypropylene, and having a basis weight of about 50 gsy, available from Veratec, Inc., Walpole, Mass.; Novonet® 149-801, a thermo-bonded grid patterned material containing about 69% rayon, about 25% polypropylene, and about 6% cotton, and having a basis weight of about 75 gsy, available from Veratec, Inc., Walpole, Mass.; Novonet® 149-191, a thermo-bonded grid patterned material containing about 69% rayon, about 25% polypropylene, and about 6% cotton, and having a basis weight of about 100 gsy, available from Veratec, Inc., Walpole, Mass.; HEF Nubtex®, a nubbed, apertured hydroentangled material, containing up to about 100% polyester, and having a basis weight of about 70 gsy, available from Veratec, Inc. Walpole, Mass.; Keybak® 951V, a dry formed apertured material, containing about 75% rayon and about 25% acrylic fibers, and having a basis weight of about 43 gsy, available from Chicopee, New Brunswick, N.J.; Keybak® 1368, an apertured material, containing about 75% rayon and about 25% polyester, and having a basis weight of about 39 gsy, available from Chicopee, New Brunswick, N.J.; Duralace® 1236, an apertured, hydroentangled material, containing about 100% rayon, and having a basis weight from about 40 gsy to about 115 gsy (where the lower basis weight materials are preferred), available from Chicopee, New Brunswick, N.J.; Duralace® 5904, an apertured, hydroentangled material, containing about 100% polyester, and having a basis weight from about 40 gsy to about 115 gsy (where the lower basis weight materials are preferred), available from Chicopee, New Brunswick, N.J.

Lamination Process

The separate paper pad layers and nonwoven synthetic fiber pad layers are laminated together to form the pads of the instant invention. The lamination can be achieved using known chemical, thermal, or mechanical means, or any combination thereof.

Chemical means employ the use of adhesives, resins, binders, and the like for adhesively laminating the layers. Thermal means employ heat so as to melt and thus fuse the synthetic fibers of the nonwoven layers to the paper layers. Mechanical means employ, e.g., pressure to compressively laminate the layers together.

The pads of the instant invention preferably are laminated by a combination of chemical, thermal, and mechanical means. Preferred laminating materials include polymers selected from the group consisting of polyethylene, polypropylene, polybutylene, polyisobutylene, and mixtures thereof. More preferred is polyethylene, an example of which is a polyethylene powder (available from Quantum Chemical as Microthene Powder).

Typically, to produce the laminated pads, a layer of the polymeric material (e.g. powdered polyethylene) is applied to one side of the paper and/or the nonwoven layer(s) which is then heated to melt the polyethylene and brought together with the other layer and compressed until laminated. Alternatively, both layers can first be brought together and heated and compressed until the two layers have been laminated. Amounts of laminating materials are on the order of about 14 g per square yard of surface area.

Once the layers have been laminated, the resulting dual layered sheets can be cut into any of a variety of suitably shaped pads using any available cutting techniques. For example, a useful pad shape and size is an oval of about 5 cm by about 7 cm. Another example is a circular pad of about 7 cm diameter.

TREATED CLEANSING PADS

The dual textured pads of the instant invention can be impregnated with, treated with, or soaked in a wide variety of medicated, cleansing, or cosmetic compositions. Especially preferred are medicated compositions containing salicylic acid. These treatment compositions and the medicated pads prepared therefrom are useful for the treatment of skin disorders such as acne and the like, and also for treating skin wrinkles and/or atrophy.

The medicated treatment pads comprise from about 5% to about 99.9% by weight of a dual textured treatment pad and from about 0.1% to about 95% of a medicated composition, more preferably from about 9% to about 30% by weight of a dual textured treatment pad and from about 70% to about 91% of a medicated composition, and most preferably from about 10% to about 20% by weight of a dual textured treatment pad and from about 80% to about 90% of a medicated composition.

Medicated Compositions

Salicylic Acid

A highly preferred component of the medicated compositions useful in preparing the treated pads of the instant invention is salicylic acid. Salicylic acid, which is also known as 2-hydroxybenzoic acid is a white crystalline powder having a melting point from about 157°–159° C. See *The Merck Index*, Tenth Edition, entry 8190, p. 1200 (1983); U.S. Pat. No. 4,514,385, to Damani et al., issued Apr. 30, 1985; and 56 *Federal Register*, pp. 41008–41020, Aug. 16, 1991; these three references are incorporated herein by reference in their entirety.

Without being limited by theory, it is believed salicylic acid provides its anti-acne benefit and its effect on skin wrinkles and/or atrophy via its keratolytic activity.

The salicylic acid of the compositions useful herein is present from about 0.01% to about 20%, more preferably from about 0.1% to about 7%, and most preferably from about 0.5% to about 2%.

Pharmaceutically-Acceptable Carriers

The medicated compositions useful in the preparation of the treated pads of the instant invention comprise a safe and effective amount of a topical pharmaceutically-acceptable carrier or diluent which can be of a variety of different forms. By "safe and effective" is meant an amount sufficient to act as a suitable vehicle for the required components and any other optional components, but not so much as to cause any side effects or skin reactions. "Pharmaceutically-acceptable" means that the carrier is suitable for topical application to the skin without causing any untoward safety or toxicity concerns. In other words, these carriers are suitable for use on mammalian skin. The typical carrier can be in the form of a hydroalcoholic system (e.g. liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems. Nonlimiting examples of the topical carrier systems useful in the present invention are described in the following four references, all of which are incorporated herein by reference in their entirety: "Sun Products Formulary", *Cosmetics & Toiletries*, vol. 105, pp. 122–139 (December 1990); "Sun Products Formulary", *Cosmetics & Toiletries*, vol. 102, pp. 117–136 (March 1987); U.S. Pat. No. 4,960,764 to Figueroa et al., issued Oct. 2, 1990; and U.S. Pat. No. 4,254,105 to Fukuda et al., issued Mar. 3, 1981.

The pharmaceutically-acceptable topical carriers, in total, typically comprise from about 0.1% to about 95% by weight of the compositions useful in the present invention, preferably from about 70% to about 91%, and most preferably from about 80% to about 90%.

An especially preferred pharmaceutically-acceptable topical carrier useful in the preparation of the pads of the instant invention is a hydroalcoholic system comprising from about 1% to about 99% of ethanol, isopropanol, or mixtures thereof, and from about 1% to about 99% of water. More preferred is a carrier comprising from about 5% to about 60% of ethanol, isopropanol, or mixtures thereof, and from about 40% to about 95% of water. Especially preferred is a carrier comprising from about 20% to about 50% of ethanol, isopropanol, or mixtures thereof, and from about 50% to about 80% of water.

pH Requirements

The pH of a formulation is an important factor in the availability of the salicylic acid and the stability of the formulation. For example, without being limited by theory, at pH values above the $pK_a$ of salicylic acid in a particular matrix, the salicylic acid would exist primarily in its ionized form and would not as readily penetrate into the skin. The following $pK_a$ values have been reported for salicylic acid: 2.98 ($H_2O$) and 7.9 (ethanol). See *CRC Handbook of Chemistry and Physics,* 57th Edition, 1976–1977, p. D-150; and *Lange's Handbook of Chemistry,* 13th Edition, 1985, p. 5–69, respectively, which are both incorporated by reference herein. Without being limited by theory, in mixed alcohol water systems, it is believed that the $pK_a$ value for salicylic acid would, in most cases fall between these extremes. An acidic formulation range is preferred for salicylic acid compositions in order to suppress ionization and enhance its penetration into the stratum corneum.

A wide variety of acids, bases, and buffers can be utilized to adjust and/or maintain the pH of the compositions useful in the instant invention. Although triethanolamine is preferred, other nonlimiting examples of materials useful for adjusting and/or maintaining the pH include sodium carbonate, sodium hydroxide, hydrochloric acid, phosphoric acid, sodium hydrogen phosphate, sodium dihydrogen phosphate, citric acid, and the like.

The compositions useful in the instant invention preferably have a pH range from about 2 to about 7, more preferably from about 2 to about 6.5, even more preferably from about 2 to about 5.5, and most preferably from about 2.5 to about 4.5.

Additional Components

The compositions useful in the preparation of the treated pads of the instant invention can include a wide variety of optional components.

Pantothenic Acid and Pantothenic Acid Derivatives

A highly preferred component of the medicated compositions useful in preparing the treated pads of the instant invention is pantothenic acid and/or a pantothenic acid derivative. Pantothenic acid, which is also known as N-(2,4-dihydroxy-3,3-dimethylbutyryl)-B-alanine, is a member of the B complex vitamins and is sometimes known as vitamin $B_3$. Pantothenic acid is a dietary essential for most mammals. The material can exist as the D(+) form, the L(–) form, and the racemate. However, only the natural D(+) form has vitamin activity. See *The Merck Index,* Tenth Edition, entry 6877, p. 1007 (1983); this reference is incorporated herein by reference in its entirety.

A variety of pantothenic acid derivatives are known and or can be synthesized. Nonlimiting examples include the alcohol, aldehyde, alcohol esters, acid esters, and the like. Especially preferred for use in the compositions of the instant invention is the alcohol derivative of pantothenic acid. This alcohol, which is also known as panthenol, pantothenol, and 2,4-dihydroxy-N-(3-hydroxypropyl)-3,3-dimethylbutanamide is a stable source of pantothenic acid activity. Like the parent acid, panthenol can exist as the D(+) form, the L(–) form, and the racemate. However, only the D(+) form has vitamin activity. The D(+) form of panthenol, which is more commonly known as dexpanthenol, is most preferred for use in the instant invention. If however, the racemate is used, it may be necessary to compensate for this factor since the racemate contains only 50% of the D(+) form. See *The Merck Index,* Tenth Edition, entry 2910, p. 426 (1983); this reference is incorporated herein by reference in its entirety.

The pantothenic acid and or pantothenic acid derivative of the compositions useful in the instant invention is present from about 0.1% to about 10%, more preferably from about 0.5% to about 5%, and most preferably from about 1% to about 3.5%.

Preferred for use in these compositions is from about 0.1% to about 10% dexpanthenol, more preferably from about 1% to about 5%, and most preferably from about 1.5% to about 3.5%.

Other Anti-Acne Agents

The compositions useful in the preparation of the treated pads of the present invention can also contain other anti-acne agents in addition to the salicylic acid.

These other anti-acne agents preferably comprise from about 0.1% to about 20% by weight of the compositions useful herein, more preferably from about 0.1% to about 10%, and most preferably from about 0.1% to about 5%. Mixtures of these additional anti-acne actives may also be used.

Examples of these other anti-acne agents include keratolytics such as sulfur, lactic acid, glycolic, pyruvic acid, urea, resorcinol, and N-acetylcysteine; retinoids such as retinoic acid and its derivatives (e.g., cis and trans); antibiotics, antimicrobials, antibacterials, antifungals, antiprotozoals, and antivirals (e.g., benzoyl peroxide, octopirox, erythromycin, tetracyclin, triclosan, azelaic acid and its derivatives, phenoxy ethanol and phenoxy propanol, ethyl acetate, clindamycin and meclocycline, triclosan, chlorhexidine, tetracycline, neomycin, miconazole hydrochloride, octopirox, parachlorometaxylenol, nystatin, tolnaftate, clotrimazole, and the like); sebostats such as flavinoids; hydroxy acids; antipruritic drugs inlcuding, for example, pharmaceutically-acceptable salts of methdilizine and trimeprazine; and bile salts such as scymnol sulfate and its derivatives, deoxycholate, and cholate.

Also, useful are non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Humectants/Moisturizers/Skin Conditioners

Another preferred optional component of the medicated compositions useful in the preparation of the treated pads of the instant invention is at least one humectant/moisturizer/skin conditioner. A variety of these materials can be employed and each can be present at a level of from about 0.1% to about 20%, more preferably from about 1% to about 10% and most preferably from about 2% to about 5%. These materials include urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, hexylene glycol and the like; polyethylene glycol; sugars and starches; sugar and starch derivatives (e.g., alkoxylated glucose); hyaluronic acid; lactamide monoethanolamine; acetamide monoethanolamine; and mixtures thereof.

Preferred humectants/moisturizers/skin conditioners useful in the compositions of the methods of the present invention are the $C_3$-$C_6$ diols and triols, and also aloe vera gel. Especially preferred is the triol, glycerol, and also aloe vera gel.

Surfactants

The compositions useful in the preparation of the treated pads of the present invention can optionally comprise one or more surfactants. The surfactants can be present at a level from about 0.1% to about 10%, more preferably from about 0.2% to about 5%, and most preferably from about 0.2% to about 2.5%. Suitable surfactants include, but are not limited to, nonionic surfactants such as polyalkylene glycol ethers of fatty alcohols, and anionic surfactants such as taurates and alkyl sulfates. Nonlimiting examples of these surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety. Examples of a broad variety of additional surfactants useful herein are described in McCutcheon's, *Detergents and Emulsifiers*, North American Edition (1986), published by Allured Publishing Corporation, which is incorporated herein by reference in its entirety.

Carboxylic Acid Copolymers

Another optional component of the compositions useful in the preparation of the treated pads of the instant invention is a carboxylic copolymer (acrylic acid copolymer). Most preferred is Carbomer 1342 (available as Carbopol 1342 from B. F. Goodrich). These polymers are more fully described in U.S. Pat. No. 4,509,949, to Huang et al., issued Apr. 5, 1985, and U.S. Pat. No. 2,798,053, to Brown, issued Jul. 2, 1957, these patents both of which are incorporated herein by reference in their entirety. Also useful are the acrylate/alkyl acrylate crosspolymers such as Acrylates/C10-C30 Alkyl Acrylate Crosspolymer (available as Pemulen TR-1 and Pemulen TR-2 from Goodrich).

These polymers comprise from about 0.025% to about 0.75%, preferably from about 0.05% to about 0.25% and most preferably from about 0.075% to about 0.175% of the compositions useful herein.

Emollients

The compositions useful in the preparation of the treated pads of the present invention can also optionally comprise at least one emollient. Examples of suitable emollients include, but are not limited to, volatile and non-volatile silicone oils, highly branched hydrocarbons, and non-polar carboxylic acid and alcohol esters, and mixtures thereof. Emollients useful in the instant invention are further described in U.S. Pat. No. 4,919,934, to Deckner et al., issued Apr. 24 1990, which is incorporated herein by reference in its entirety.

The emollients can typically comprise in total from about 1% to about 50%, preferably from about 1% to about 25%, and more preferably from about 1% to about 10% by weight of the compositions useful in the present invention.

Sunscreens

The compositions useful in the preparation of the treated pads of the present invention can also optionally comprise at least one sunscreening agent. A wide variety of one or more sunscreening agents are suitable for use in the present invention and are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety.

Preferred among those sunscreens which are useful in the compositions of the instant invention are those selected from the group consisting of ethylhexyl p-methoxycinnamate, octocrylene, octyl salicylate, oxybenzone, and mixtures thereof.

Other useful sunscreens include the solid physical sunblocks such as titanium dioxide (micronized titanium dioxide, 0.03 microns), zinc oxide, silica, iron oxide and the like. Without being limited by theory, it is believed that these inorganic materials provide a sunscreening benefit through reflecting, scattering, and absorbing harmful UV, visible, and infrared radiation.

Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens.

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp.

38206–38269, Aug. 25, 1978, which is incorporated herein by reference in its entirety.

Other Optional Components

A variety of additional ingredients can be incorporated into the compositions useful in the preparation of the treated pads of the present invention. Non-limiting examples of these additional ingredients include other vitamins and derivatives thereof (e.g., ascorbic acid, vitamin E, tocopheryl acetate, and the like); thickening agents (e.g. polyacrylamide and $C_{13-14}$ isoparaffin and laureth-7, available as Sepigel from Seppic Corporation); resins; gums; cationic polymers and thickeners (e.g., cationic guar gum derivatives such as guar hydroxypropyltrimonium chloride and hydroxypropyl guar hydroxypropyltrimonium chloride, available as the Jaguar C series from Rhone-Poulenc; copolymers of acrylamide and a cationic acrylate (available as Salcare SC92 from Allied Colloid); emulsifiers; polymers for aiding the film-forming properties and substantivity of the composition (such as a copolymer of eicosene and vinyl pyrrolidone, an example of which is available from GAF Chemical Corporation as Ganex V-220®); preservatives for maintaining the antimicrobial integrity of the compositions; skin penetration aids such as DMSO, 1-dodecyl-azacycloheptan-2-one (available as Azone from the Upjohn Co.) and the like; artificial tanning agents such as dihydroxyacetone and the like; skin bleaching (or lightening) agents including but not limited to hydroquinone, ascorbic acid, kojic acid and sodium metabisulfite; antioxidants; chelators and sequestrants; and aesthetic components such as fragrances, pigments, colorings, essential oils, skin sensates, astringents, skin soothing agents, skin healing agents and the like, nonlimiting examples of these aesthetic components include clove oil, menthol, camphor, eucalyptus oil, eugenol, menthyl lactate, witch hazel distillate, allantoin, bisabalol, dipotassium glycyrrhizinate and the like.

Methods for Treating Acne

The present invention also relates to a method for treating acne in mammalian skin. Such a method comprises topically applying to the skin a dual textured pad for delivering an effective amount of a composition containing an effective amount of an anti-acne composition. The term "effective amount", as used herein, means an amount sufficient to provide an anti-acne benefit. Typically, an effective coating of the skin is from about 0.01 mg salicylic acid or composition of the present invention/$cm^2$ skin to about 5 mg salicylic acid or composition of the present invention/$cm^2$ skin. The composition can be continually applied at appropriate intervals, preferably about once or twice a day until the acne subsides.

Methods for Regulating Wrinkles and/or Skin Atrophy in Mammalian Skin

The present invention also relates to a method for regulating wrinkles and/or atrophy in mammalian skin. Such a method comprises topically applying to the skin a dual textured pad for delivering a safe and effective amount of a medicated composition useful for treating skin wrinkles and/or atrophy. The term "effective amount", as used herein, means an amount sufficient to provide a therapeutic effect. Typically, an effective coating of the skin is from about 0.01 mg salicylic acid or composition of the present invention/$cm^2$ skin to about 5 mg salicylic acid or composition of the present invention/$cm^2$ skin.

A preferred method of treating the skin is via chronic topical application. By "chronic" application, it is meant herein that the period of topical application may be over the lifetime of the subject thereby resulting in regulation of wrinkles and/or atrophy in mammalian skin.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Example I

A dual textured treatment pad of the present invention is made from the following materials.

Paper Layer

Embossed airlaid paper, 0.035 in. (0.089 cm) caliper, and basis weight of 71 gsy.[1]

Nonwoven Layer

Apertured, hydroentangled 50% rayon, 50% polyester nonwoven fabric of basis weight 43 gsy, having apertures of about 1.0 $mm^2$ which comprise about 35% of the surface area of the fabric.[2]

Lamination Material

Polyethylene Powder.[3]

[1] Available as Airtex® 382 from James River, Green Bay, Wis.
[2] Available as HEF 140-037 from Veratec, Walpole, Mass.
[3] Available as Microthene Powder from Quantum Chemicals.

The two layers are laminated together by laying the polyethylene powder (about 14 grams per square yard) on the paper layer which is passed through a convection oven at around 190° C. until the polyethylene powder is melted. The nonwoven layer is then laid upon the emerging paper layer which is then passed through a nip roll to join the layers. The resulting dual textured fabric is then cut into oval pads of about 5 cm by about 7 cm.

The resulting oval pads are suitable for saturation with any of the medicated compositions described in Examples VI–X. The resulting medicated pads are suitable for the treatment of acne, or alternatively to regulate skin wrinkles and/or skin atrophy.

Example II

A dual textured treatment pad of the present invention is made from the following materials.

Paper Layer

Embossed airlaid paper, 0.035 in. (0.089 cm) caliper and basis weight of 71 gsy.[1]

Nonwoven Layer

Blue apertured, hydroentangled 100% polyester nonwoven fabric of basis weight 70 gsy, having apertures of about 0.24 $mm^2$ which comprise about 9% of the surface area of the fabric, and having raised nubs.[2]

Lamination Material

Polyethylene Powder[3]

[1] Available as Airtex® 382 from James River, Green Bay, Wis.
[2] Available as HEF Nubtex® from Veratec, Walpole, Mass.
[3] Available as Microthene Powder from Qauntum Chemicals.

The two layers are laminated together by laying the polyethylene powder (about 14 g per square yard) on the paper layer which is passed through a convection oven at around 190° C. until the polyethylene powder is melted. The nonwoven layer is then laid upon the emerging paper layer which is then passed through a nip roll to join the layers. The resulting dual textured fabric is then cut into oval pads of about 5 cm by about 7 cm.

The resulting oval pads are suitable for saturation with any of the medicated compositions described in Examples VI–X. The resulting medicated pads are suitable for the treatment of acne, or alternatively to regulate skin wrinkles and/or skin atrophy.

Example III

A dual textured treatment pad of the present invention is made from the following materials.

Paper Layer
  Embossed airlaid paper, 0.035 in. (0.089 cm) caliper and basis weight of 71 gsy.[1]

Nonwoven Layer
  Apertured 75% rayon, 25% polyester nonwoven fabric of basis weight 39 gsy, having apertures of about 1.0 mm$^2$ which comprise about 26% of the surface area of the fabric.[2]

Lamination Material
  Polyethylene Powder[3]

[1]Available as Walkisoft® from Walkisoft U.S.A., Mount Holly, N.C.
[2]Available as Keybak® 1368 from Chicopee, New Brunswick, N.J.
[3]Available as Microthene Powder from Quantum Chemicals.

The two layers are laminated together by laying the polyethylene powder (about 14 grams per square yard) on the paper layer which is passed through a convection oven at around 190° C. until the polyethylene powder is melted. The nonwoven layer is then laid upon the emerging paper layer which is then passed through a nip roll to join the layers. The resulting dual textured fabric is then cut into oval pads of about 5 cm by about 7 cm.

The resulting oval pads are suitable for saturation with any of the medicated compositions described in Examples VI–X. The resulting medicated pads are suitable for the treatment of acne, or alternatively to regulate skin wrinkles and/or skin atrophy.

EXAMPLE IV

A dual textured treatment pad of the present invention is made from the following materials.

Paper Layer
  Embossed airlaid paper, 0.035 in. (0.089 cm) caliper and basis weight of 71 gsy.[1]

Nonwoven Layer
  Thermo-bonded grid patterned 69% rayon, 25% polypropylene, 6% cotton fabric of basis weight 75 gsy and two discrete regions of mean thickness of about 0.079 cm and about 0.018 cm, respectively.[2]

Lamination Material
  Polyethylene Powder[3]

[1]Available as Walkisoft® from Walkisoft U.S.A., Mount Holly, N.C.
[2]Available as Novonet® 149-801 from Veratec, Walpole, Mass.
[3]Available as Microthene Powder from Quantum Chemicals.

The two layers are laminated together by laying the polyethylene powder (about 14 grams per square yard) on the paper layer which is passed through a convection oven at around 190° C. until the polyethylene powder is melted. The nonwoven layer is then laid upon the emerging paper layer which is then passed through a nip roll to join the layers. The resulting dual textured fabric is then cut into circular pads of about 7 cm diameter.

The resulting circular pads are suitable for saturation with any of the medicated compositions described in Examples VI–X. The resulting medicated pads are suitable for the treatment of acne, or alternatively to regulate skin wrinkles and/or skin atrophy.

Example V

A dual textured treatment pad of the present invention is made from the following materials.

Paper Layer
  Embossed airlaid paper, 0.035 in. (0.089 cm) caliper and basis weight of 71 gsy.[1]

Nonwoven Layer
  50% Rayon Fiber (1.5 inches and denier=2)
  30% Polyester Fiber (2 inches and denier=6)
  20% Polypropylene Fiber (2 inches and denier=2)
  Styrene-butadiene resin (styrene to butadiene ratio of 45:55).[1]

Lamination Material
  Polyethylene Powder[2]

[1]Available as Walkisoft® from Walkisoft U.S.A., Mount Holly, N.C.
[2]Available as 76 RES 4305 from UNOCAL 76.
[3]Available as Microthene Powder from Quantum Chemicals.

The nonwoven layer is prepared by carding the fibers to form layers of rayon, polyester, and polypropylene fibers. These layers are then hydrodentangled using conventional methodologies to form an apertured nonwoven fabric having apertures of about 0.5 mm$^2$ which comprise about 12% of the surface area of the fabric. The apertured fabric is then treated with the styrene-butadiene resin and passed through a series of drying cans to cure the resin and dry the nonwoven fabric.

The resulting nonwoven layer is laminated to the paper layer by laying the polyethylene powder (about 14 grams per square yard) on the paper layer which is passed through a convection oven at around 190° C. until the polyethylene powder is melted. The nonwoven layer is then laid upon the emerging paper layer which is then passed through a nip roll to join the layers. The resulting dual textured fabric is then cut into oval pads of about 5 cm by about 7 cm.

The resulting oval pads are suitable for saturation with any of the medicated compositions described in Examples VI–X. The resulting medicated pads are suitable for the treatment of acne, or alternatively to regulate skin wrinkles and/or skin atrophy.

Examples VI–X

Medicated Compositions

The following medicated compositions are prepared by combining the following components utilizing conventional mixing techniques. These compositions are useful for saturating the dual textured pads of the instant invention (e.g., Examples I–V) for the preparation of medicated pads. The resulting medicated pads are thus suitable for the treatment of acne, or alternatively to regulate skin wrinkles and/or skin atrophy.

| Ingredients | % Weight | | | | |
|---|---|---|---|---|---|
| | VI | VII | VIII | IX | X |
| Deionized Water | qs 100 | qs 100 | qs 100 | qs 100 | qs 100 |
| Ethanol (SD 40B Alcohol) | 35.0 | 35.0 | 35.0 | 20.0 | 35.0 |
| Salicylic Acid | 2.0 | 2.0 | 2.0 | 0.5 | 2.0 |
| Dexpanthenol | — | 3.0 | — | — | 3.0 |
| Glycerol | — | 2.0 | 2.0 | — | — |
| Aloe Vera Gel | 0.5 | — | 1.0 | 0.5 | — |
| Menthol | — | — | — | 0.05 | — |
| Witch Hazel Distillate | — | — | — | 5.0 | — |
| Na Methyl Cocoyl Taurate or Na Methyl Oleoyl Taurate | — | — | — | 1.0 | — |
| Isoceteth-20 | — | — | — | — | 2.0 |
| Quaternium-22 | — | — | — | 1.0 | — |
| Disodium EDTA | — | 0.005 | 0.005 | 0.005 | 0.005 |
| Triethanolamine, 99% | — | 0–1.0 | 0–1.0 | — | 0–1.0 |

In a suitable vessel the salicylic acid is dissolved in the ethanol with stirring. In a separate vessel the remaining ingredients except for the triethanolamine (where used) are dissolved in the water with stirring. The resulting alcohol and water solutions are then combined with mixing. Next, sufficient triethanolamine (where used) is added as needed to adjust the pH to between about 2.5 to about 4.5.

These compositions are useful for preparing medicated pads by saturating the dual textured pads of the instant invention.

What is claimed is:

1. A dual textured laminated treatment pad comprising:
   (a) at least one paper layer having a basis weight from about 35 gsy to about 155 gsy and a thickness from about 0.045 cm to about 0.30 cm, said paper layer comprising cellulosic fibers selected from the group consisting of wood pulp fibers, cotton fibers, hemp fibers, jute fibers, flax fibers, and mixtures thereof, and
   (b) at least one synthetic fiber, nonwoven layer having a basis weight from about 20 gsy to about 105 gsy, having a repeating pattern comprising at least two adjacent delineated regions simultaneously not having the same mean thickness, wherein the first of said at least two adjacent delineated regions has a mean thickness from about 0.025 cm to about 0.30 cm and the second of said at least two adjacent delineated regions has a mean thickness from about 0.010 cm to about 0.050 cm,
   whereby said paper layer is positioned parallel to and in contact with said synthetic nonwoven layer.

2. A pad according claim 1 wherein said synthetic fiber, nonwoven layer comprises synthetic fibers selected from the group consisting of acrylic fibers, nylon fibers, polyester fibers, polypropylene fibers, rayon fibers, and mixtures thereof.

3. A pad according to claim 2 wherein said synthetic fiber, nonwoven layer further comprises from about 0.01% to about 10% of cellulosic fibers selected from the group consisting of wood pulp fibers, cotton fibers, hemp fibers, jute fibers, flax fibers, and mixtures thereof.

4. A pad according to claim 2 wherein said paper layer has a basis weight from about 60 gsy to about 100 gsy and a thickness from about 0.070 cm to about 0.11 cm and said synthetic fiber, nonwoven layer has a basis weight from about 30 gsy to about 80 gsy and a thickness of said first region from about 0.035 cm to about 0.095 cm and a thickness of said second region from about 0.015 cm to about 0.025 cm.

5. A pad according to claim 4 which further comprises a polymeric material for laminating said paper layer and said synthetic fiber nonwoven layer.

6. A pad according to claim 5 wherein said polymeric material is selected from the group consisting of polyacrylate, polyethylene, polypropylene, polybutylene, polyisobutylene, polyurethane, polyvinyl acetate, and mixtures thereof.

7. A pad according to claim 6 wherein said polymeric material is polyethylene.

8. A pad according to claim 7 wherein said synthetic fiber, nonwoven layer further comprises a polymeric binding resin.

9. A pad according to claim 8 wherein said polymeric resin comprises monomers selected from the group consisting of styrene monomers, derivatized styrene monomers, butadiene monomers, derivatized butadiene monomers, and mixtures thereof.

10. A pad according to claim 9 wherein said polymeric resin is a styrene-butadiene polymer.

11. A pad according to claim 2 which further comprises nubs which project out of the plane of the first of said at least two adjacent delineated regions of said synthetic fiber, nonwoven layer.

12. A medicated pad comprising:
   (a) from about 10% to about 20% by weight of a dual textured laminated treatment pad according to claim 1, and
   (b) from about 80% to about 90% of a medicated composition.

13. A medicated pad according to claim 12 wherein said medicated composition comprises:
   (a) from about 0.01% to about 20% of salicylic acid,
   (b) from about 5% to about 60% of an alcohol selected from ethanol, isopropanol, or mixtures thereof, and
   (c) from about 40% to about 95% of water,
   wherein said composition has a pH from about 2 to about 7.

14. A method of treating acne in mammalian skin comprising treating the skin with the medicated pad of claim 13.

15. A method of regulating skin wrinkles and/or atrophy in mammalian skin comprising treating the skin with the medicated pad of claim 13.

* * * * *